US006150540A

United States Patent [19]

[11] Patent Number: 6,150,540
[45] Date of Patent: Nov. 21, 2000

Uckun et al.

[54] VERSATILE INTERMEDIATE FOR ANNONACEOUS ACETOGENINS

[75] Inventors: Fatih M. Uckun, White Bear Lake; Keqiang Li, St. Paul; Shyi-Tai Jan, Roseville, all of Minn.

[73] Assignee: Hughes Institute, Roseville, Minn.

[21] Appl. No.: 09/184,792

[22] Filed: Nov. 2, 1998

[51] Int. Cl.[7] ........................ C07D 307/08; C07D 307/04

[52] U.S. Cl. ............................................ 549/472; 549/502

[58] Field of Search ...................................... 549/472, 502

[56] References Cited

U.S. PATENT DOCUMENTS

| | | | |
|---|---|---|---|
| 5,677,467 | 10/1997 | Hoye et al. | 549/320 |
| 5,717,113 | 2/1998 | McLaughlin et al. | 549/347 |
| 5,739,358 | 4/1998 | Hoye et al. | 549/320 |

OTHER PUBLICATIONS

Makabe, H. et al. : Total synthesis of (8' R) and (8' S) corossoline. Heterocycles, vol. 43, pp. 2229–2248, 1996.

Li, K. et al.: Stereocontrolled synthesis of the tetrahydrofuran unit of annonaceous acetogenins. Tetrahed. Lett. vol. 39, pp. 2063–2066, Apr. 1998.

Gesson, J. et al., "Synthesis of the THF Moiety of Annonacin Based on Aldolisation and Bayer—Villiger Oxidation", *Tetrahedron Letters*, vol. 38, No. 33, pp. 5811–5814 (1997).

Jan, S. et al., "Stereoselective Synthesis of a Versatile Intermediate for the Total Synthesis of Mono– and Bis–THF Containing Annonaceous Acetogenins", *Tetrahedron Letters*, vol. 40, pp. 193–196 (1999).

Li, K. et al., "Stereocontrolled Synthesis of the Tetrahydrofuran Unit of Annonaceous Acetogenins", *Tetrahedron Letters*, vol. 39, pp. 2063–2066 (1998).

Zhang, H. et al., "Asymmetric Dihydroxylation–Haleotherification Strategy for the Synthesis of Tetrahydrofuran–Containing Acetogenins", *J. Org. Chem.*, vol. 63, pp. 2049–2053 (1998).

Jolad, S.D., Uvaricin, a New Antitumor Agent from Uvaria accuminata (Annonaceae), J. Org. Chem., 1982, 47, 3151–53.

Hanson, R.M.; Sharpless, K.B., Procedure for the Catalytic Asymmetric Epoxidation of Allylic Alcohols in the Presence of Molecular Sieves, J. Org. Chem., 1986, 51, 1922–25.

Abushanab, E.; et al., The Chemistry of L–Ascorbic and D–Isoascorbic Acids. 1. The Preparation of Chiral Butanetriols and –tetrols, J. Org. Chem., 1988, 53, 2602–08.

Krief, A.; et al., Stereoselective Synthesis of Methyl (1R)Trans– and (1R)Cis—Hemicaronaldehydes from Natural Tartaric Acid: Application to the Synthesis of S–Bioallethrin and Deltamethrin Insecticides, Tetrahedron, 1989, 45, 3039–52.

Alkofahi, A.; et al., Gigantecin: A Novel Antimitotic and Cytotoxic Acetogenin, With Nonadjacent Tetrahydrofuran Rings, from Goniothalamus Giganteus (Annonaceae), Experientia, 1990, 46, 539–41.

Bertrand, P.; Gesson, J–P., Approach to the Synthesis of Annonaceous Acetogenins From D–Glucose, Tetrahedron Letters, 1992, 33, 5177–80.

Harmange, J–C.; et al., Stereocontrolled Synthesis of 2,5–Linked Monotetrahydrofuran Units of Acetogenins, Tetrahedron Letters, 1992, 33, 5749–52.

Gu, Z.; et al., Gonionenin: A New Cytotoxic Annonaceous Acetogenin From Goniothalamus Giganteus and the Conversion on Mono–THF Acetogenins to Bis–THF Acetogenins, J. Org. Chem., 1994, 59, 3472–79.

Koert, U.; et al., A Convergent Synthesis of 2,5–Trans–Linked Oligo (Terahydrofuran)s: Potential Building Blocks for a Polyether Helix With Ion Channel Activity, Angew. Chem. Int. Ed. Engl., 1994, 33, 1180–82.

Koert, U., Stereoselective Synthesis of Oligo–Tetrahydrofurans, Synthesis, Feb. 1995, 115–32.

Hidefumi, M.; et al., Total Synthesis of Solamin and Reticulatacin, J. Chem. Soc. Perkin Trans. 1, 1994, 1975–81.

Yao, Z–J.; Wu, Y–L., Total Synthesis of (10E, 15R, 16S, 19S, 20S, 34R)—Corossoline, Tetrahedron Letters, 1994, 35, 157–60.

Yao, Z–J.; Wu, Y–L., Synthetic Studies Toward Mono–THF Annonaceous Acetogenins: A diastereoselective and Convergent Approach to Corossolone and (10RS)—Corossoline, J. Org. Chem., 1995, 60, 1170–76.

Figadere, B., Syntheses of Acetogenins of Annonaceae: A New Class of Bioactive Polyketides, Acc. Chem. Res., 1995, 28, 359–65.

Hoye, T.R.; Ye, Z., Highly Efficient Synthesis of the Potent Antitumor Annonaceous Acetogenin (+)—Parviflorin, J. Am. Chem. Soc., 1996, 118, 1801–02.

Zeng, L.; Recent Advances in Annonaceous Acetogenins, Natural Product Reports, 1996, 275–306.

Figadere, B.; et al., Replicative Chirons: Stereoselective Synthesis of Oligo–Tetrahydrofuranic Lactones Via C–Glycosylation With [(Trimethylsily)oxy]furan, J. Org. Chem., 1997, 62, 3428–29.

Gu, Z–M.; et al., Chapter Eleven—Annonaceous Acetogenins, Phytochemistry of Medicinal Plants, Arnason et al., Plenum Press, N.Y., 1995, 249–310.

*Primary Examiner*—C. S. Aulakh
*Attorney, Agent, or Firm*—Merchant & Gould P.C.

[57] ABSTRACT

A tetrahydrofuran (THF) epoxide and method of its preparation according to a novel stereoselective synthetic method. The compounds of the invention are used to prepare therapeutically active mono-THF and bis-THF containing Annonaceous Acetogenins.

14 Claims, No Drawings

VERSATILE INTERMEDIATE FOR ANNONACEOUS ACETOGENINS

FIELD OF THE INVENTION

The invention relates to a novel compounds, particularly a tetrahydrofuran (THF) epoxide prepared according to a novel stereoselective synthetic method. The compounds of the invention can be used to prepare therapeutically active mono-THF and bis-THF containing Annonaceous Acetogenins.

BACKGROUND OF THE INVENTION

Since the first discovery of uvaricin in 1982[1], more than 220 annonaceous acetogenins have been reported. Considerable attention has been paid to this class of naturally occurring polyketide-derived fatty acids due to their pleiotropic biological activities[2], including their immunosuppressive and anti-neoplastic properties. Acetogenins are optically pure compounds frequently containing 1-3 tetrahydrofuran (THF) rings in the center of a long hydrocarbon chain. The stereochemistry of the THF rings may affect the activity of acetogenins since it has been noticed that different stereoisomers of acetogenins display strikingly different biological activity profiles. However, very little is known about the structure-activity relationships contributing to these differences.

Earlier reports described schemes for total synthesis of mono-THF and bis-THF acetogenins.[3] However, very few synthetic strategies yielding the central core THF-unit of mono-THF containing acetogenins are stereoselective and therefore require chromatographic separation of the key intermediates.[4]

[1] Jolad, S. D.; Hoffinan, J. J.; Schram, K. H.; Tempesta, M. S.; Kriek, G. R.; Bates, R. B.; Cole, J. R. *J. Org. Chem.* 1982, 47, 3151.

[2] Zeng, L.; Ye, Q.; Oberlies, N. H.; Shi, G.; Gu, Z.-M.; He, K.; McLaughlin, J. L. *Natural Product Reports*, 1996, 275 and references cited therein.

[3] a) Figadere, B.; Peyrat, J.-F.; Cave, A. *J. Org. Chem.* 1997, 62, 3248 and references cited therein. b) Hoye, T. R.; Ye, Z. *J. Am. Chem. Soc.* 1996, 118, 1801. c) Figadere, B. *Acc. Chem. Res.* 1995, 28, 359 and references cited therein.

[4] a) Gesson, J.-P.; Bertrand, P. *Tetrahedron Lett.* 1992, 33, 5177. b) Harmange, J.-C.; Figadere, B. Cave, A. *Tetrahedron Lett.* 1992, 33, 5749. c) Makabe, H.; Tanaks, A.; Oritani, T. *J. Chem. Soc. Perkin Trans. I*, 1994, 1975. d) Wu, Y.-L.; Yao, Z.-J. *Tetrahedron Lett.* 1994, 35, 157. e) Wu, Y.-L.; Yao, Z.-J. *J. Org. Chem.* 1995, 60,1170.

An efficient and stereocontrolled approach to synthesize the central core THF-unit of mono-THF containing acetogenins which allows each stereogenic center around the THF ring to be controlled is reported in copending patent application U.S. Ser. No. 09/009,057. We have now discovered a novel stereoselective synthetic method for producing the epoxy THF precursor for the total synthesis for mono-THF and bis-THF containing acetogenins.

SUMMARY OF THE INVENTION

Accordingly the present invention is directed to a stereoselective synthesis of a $C_{16}$–$C_{34}$ unit of a $C_{37}$ acetogenin or the $C_{14}$–$C_{32}$ unit of a $C_{35}$ acetogenin. The invention also includes novel versatile precursors which are key in the synthesis of the therapeutically active mono- or bis-THF acetogenins.

The present invention includes as novel, versatile compounds for the total synthesis of the above acetogenins stereoisomeric compounds of the formulae (I) or (XII):

(I)

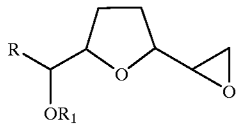

(XII)

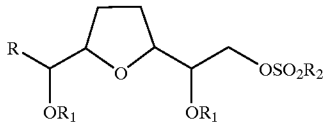

where R is s hydrocarbon of the formula $H_{2n+1}C_n$, where n is at least 1, and preferably n is about 8 to about 15. $R_1$ is selected from H, lower alkyl, or a hydroxy protecting group such as alkyl ether, silyl ether, acetal, and acetate. $R_2$ is H, aryl, or alkyl, preferably phenyl or methyl phenyl, particularly paramethylphenyl. When $R_2$ is alkyl, lower alkyls having 6 or fewer carbon atoms are preferred. A particular compound of choice in this case is the compound of the formula I or XII where R is $H_{25}C_{12}$.

The present invention also includes a process for preparing the intermediate of the formula I which includes the steps of:

(a) reacting an aliphatic aldehyde of the formula (II)

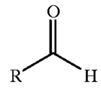

with a vinyl magnesium halide, such as vinyl magnesium bromide, to from an allylic alcohol (III);

(III)

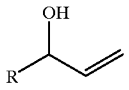

(b) reacting the allylic alcohol (III) with triethyl orthoacetate in the presence of a catalytic amount of acid such as propionic acid to form a γ,δ-unsaturated ethyl ester of formula (IV) via the Johnson Claisen rearrangement;[5]

(IV)

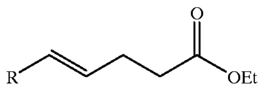

(c) extending the carbon chain of the γ,δ-unsaturated ethyl ester of formula (IV) via the four-step reaction sequence commonly used in Sharpless asymmetric epoxidation (AE) and as described in Rossiter et. al.[6], to form an allylic alcohol of formula (VIII);

(VIII)

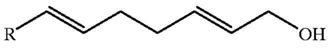

(d) converting allylic alcohol (VIII) to an epoxy alcohol of formula (IX) via Sharpless asymmetric epoxidation (AE)[7]. The chosen chiral auxiliary provides a desired stereochemistry, for example using diisopropyl L-tartrate (L-(+)-DIPT);

[5] Trust et.al., 1988, *Organic Synth. Coil.* 6:606.
[6] Rossitier B. E., 1985, In: *Asymmetric Synthesis*, Academic Press, Orlando, PP.193–246.
[7] Rossitier, id.

(IX)

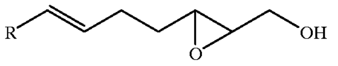

(e) converting the primary alcohol of the epoxy alcohol (IX) to a leaving group such as tosylate or mesylate, for example converting OH to $OSO_2R_2$, where $R_2$ is aryl or alkyl of formula (X):

(X)

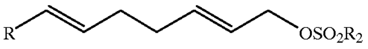

(f) forming the epoxide of formula (XI), for example, by subjecting (X) to Sharpless asymmetric dihydroxylation (ADH) using AD mix-β;

(XI)

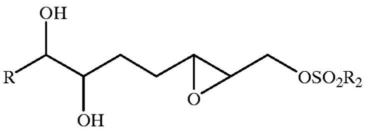

(g) opening the epoxide ring by acid catalyzed reaction and simultaneously 5-exo cyclizaton of the epoxide (XI) to form the desired THF unit of formula (XII); and (XII)

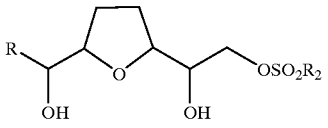

(h) treating the THF-containing compound (XII) with a base, such as $K_2CO_2$ in methanol to form the epoxy THF compound of formula (I):

(I)

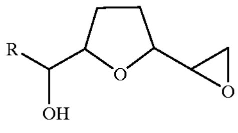

DETAILED DESCRIPTION

The following terms used throughout the present application have the following meanings:

The term "aryl" denotes an aromatic group and is particularly a phenyl or a substituted phenyl group wherein the substituents are those that are typically used in organic chemistry or an aromatic ring such as, for example, alkyl, alkoxy, halo or nitro.

The term "alkyl" denotes a straight or branched hydrocarbon chain and with the term "lower" includes such straight or branched hydrocarbon chain having from 1 to about 6 carbon atoms. As a preferred embodiment, chains from 1 to 4 carbon atoms are included. These include as examples, methyl, ethyl, propyl, isopropyl, butyl, secondary butyl, t-butyl, and the like.

The term "alkoxy" refers to an alkyl moiety connected to an oxygen atom depicted by the formula OR, where R is an alkyl chain as defined above. Preferred alkoxy groups include methoxy, ethoxy, propoxy, butoxy, and the corresponding branched chain alkoxy groups of the propoxy and butoxy groups.

The term "halo" includes the halogen family and particularly fluoro, chloro, bromo, and iodo. A preferred halo substituent is chloro.

The term "hydroxy protecting group" means any group capable of protecting a hydroxyl group and capable of being easily removed including such protecting groups as alkyl ether, silyl ether, acetyl, and acetate.

Useful compounds of the invention include compounds having the formula I or XII:

(I)

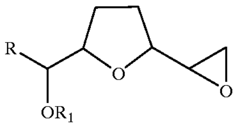

(XII)

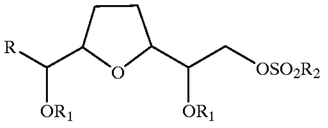

where R is a hydrocarbon of the formula $H_{2n+1}C_n$, where n is at least 1, and preferably n is in the range of about 8 to about 15. A particularly preferred compound is one where R is $H_{25}C_{12}$. $R_1$ is selected from the group consisting of H and various hydroxy protecting groups such as alkyl ether, silyl ether, acetal, and acetate. Compounds I and XII where $R_1$ is H contain hydroxyls which are beneficially protected with the hydroxy protecting groups. $R_2$ is alkyl or aryl, forming, for example, a leaving group such as mesylate or tosolate.

I

The synthesis of the novel intermediates of the present invention by a stereoselective method illustrated by way of example in Scheme 1, below.

Scheme 1:

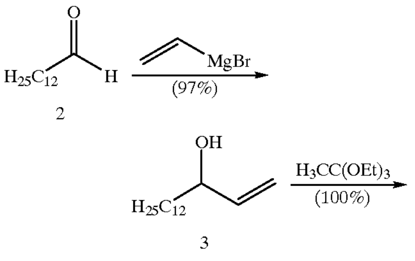

2

3

-continued

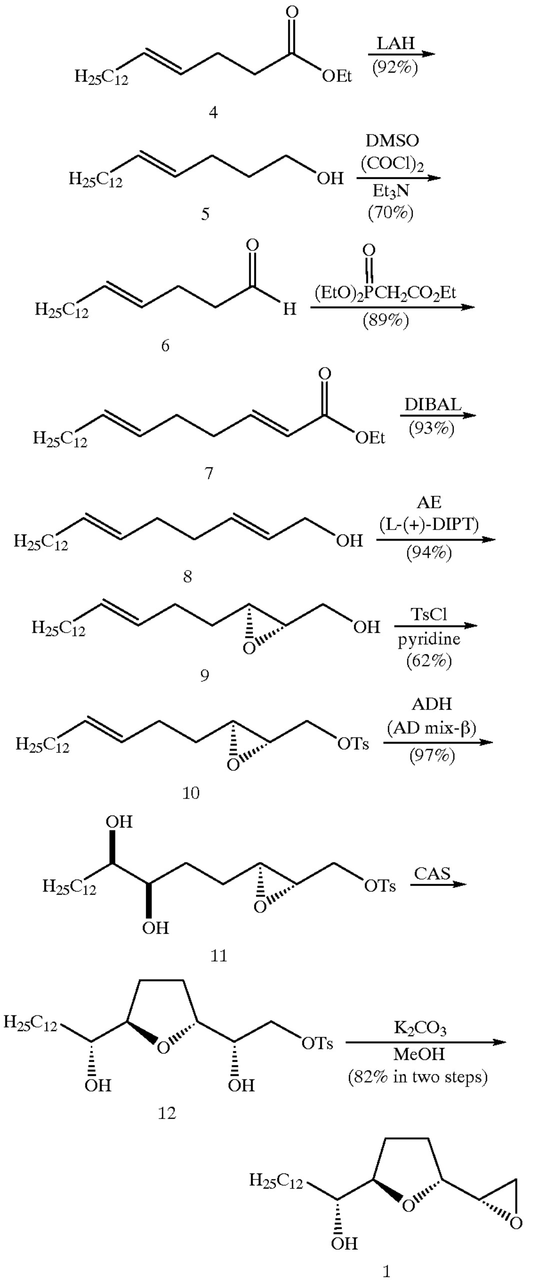

The commercially available, long chain aliphatic aldehyde, tridecanl 2, was extended to an γ,δ-unsaturated ethyl ester 4 by a two step reaction sequence, as described in Wang et.al., 1992.[8] Reaction with vinyl magnesium bromide afforded the allylic alcohol 3 followed by reaction with triethyl orthoacetate and a catalytic amount of propionic acid to form the ester 4 via the Johnson Claisen rearrangement.[9] The carbon chain of the γ,δ-unsaturated ethyl ester 4 was further extended by a four step reaction sequence, commonly used in the application of Sharpless asymmetric epoxidation (AE) to form the allylic alcohol 8.[10] The allylic alcohol 8 was converted to the epoxy alcohol 9 by Sharpless asymmetric epoxidation (AE) using diisopropyl L-tartrate (L-(+)-DIPT) as the chiral auxiliary.[11] The primary alcohol in 9 was converted to tosylate 10 which was subjected to Sharpless asymmetric dihydroxylation (ADH) by AD mix-β to form 11.[12] The camphor sulfonic acid (CSA) catalyzed epoxide ring opening and simultaneously 5-exo cyclization of 11 afforded the desired THF unit in 12. Treatment of 12 with $K_2CO_3$ in methanol afforded the expoxy THF 1.[13]

[8] Wang et.al., 1992, *Tetrahedron Lett.* 33:6407–6410.
[9] Trust et.al., 1988, *Organic Synth. Coll.* 6:606.
[10] Rossiter, B. E., Supra.
[11] Rossiter, Id.
[12] Kolb et.al., 1994, *Chem. Rev.* 94:2483–2547.
[13] See Example 1 for the data characterizing compound 1.

Thus, compound 1 was synthesized in a straightforward fashion from the commercially available tridecanal 2 in 11 steps with an overall yield of 24%. The requisite configurations of the stereogenic centers in 1 were established by Sharpless asymmetric epoxidation and Sharpless asymmetric dihydroxylation. Formation of the 2,5-disubstituted THF-ring was accomplished by acid catalyzed epoxide ring opening and 5-exo cyclization reaction.

The epoxy THF 1 corresponding to the $C_{16}$–$C_{34}$ unit of a $C_{37}$ acetogenin or the $C_{14}$–$C_{32}$ unit of a $C_{35}$ acetogenin is a versatile synthetic precursor for mono- and Bis-THF containing acetogenins. The epoxide group in 1 can be reacted with various nucleophiles to form a desired acetogenin.

In addition, the stereogenic centers in THF 1 can easily be altered because: (i) the antipodes of the chiral auxiliaries used in the asymmetric induction steps are commercially available; and (ii) the absolute configuration of the epoxide stereogenic center can be reversed by converting the secondary hydroxy group of the vicinal diol, instead of the primary hydroxy group, to a leaving group for the epoxide ring closure.

Thus, the present invention provides an efficient procedure for the stereoselective synthesis of a versatile precursor for the total synthesis of mono- and bis-THF containing Annonaceous acetogenins. This synthetic approach offers several advantages over previously described strategies. First, the synthetic scheme is stereoselective. Secondly, the stereogenic centers of the compounds of the invention can be easily altered during synthesis by the choice of auxiliaries which are commercially available. Furthermore, absolute configuration of the epoxide stereogenic centers can be reversed.

EXAMPLES

The invention may be further understood by reference to the following examples, which are exemplary in nature, and not limiting of the invention.

Materials and Methods

Proton nuclear magnetic resonance ($^1$H-NMR) spectra were recorded at 300 MHz (Varian-300). Carbon-13 magnetic resonance ($^{13}$C-NMR) were recorded at 75.5 MHz (Varian-300). Chemical shifts are reported in parts per million (ppm) upfield from an internal reference of tetramethylsilane and coupling constants (J values) are reported in hertz (Hz). The data are reported as follows: chemical shift; number of protons; multiplicity (s=singlet, d=doublet, t=triplet, q=quartet, dd=doublet of doublets, etc.); coupling constants. Unresolved resonances and resonances complicated by non-first order splitting are reported as multiplet (m) or broadened (br), as appropriate.

All moisture-sensitive reactions were performed in oven-dried glassware under a nitrogen atmosphere maintained by rubber septa. Moisture-sensitive reagents were transferred using standard syringe and cannulation techniques.

Ethyl ether and tetrahydrofuran were distilled from sodium/benzophenone immediately prior to use. Dichloromethane was distilled from calcium hydride and used immediately. Organic amines were distilled from calcium hydride and stored over potassium hydroxide.

Flash column chromatography was performed using Baker silica gel. For binary solvent systems, the proportion of solvents is given as volume/volume ratio.

Example 1

The synthesis of a novel intermediates of the present invention by a stereoselective method illustrated by way of example in Scheme 1, below.

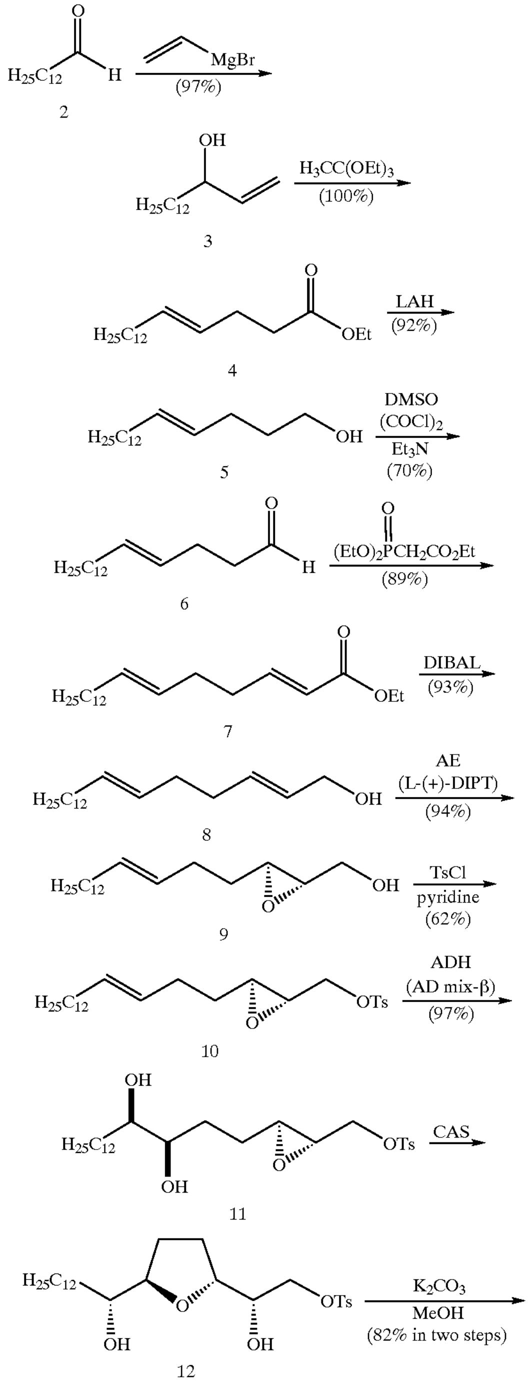

-continued

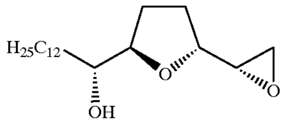

1

The commercially available, long chain aliphatic aldehyde, tridecanl 2, was extended to an γ,δ-unsaturated ethyl ester 4 by a two step reaction sequence, as described in Wang et.al., 1992.[14] Reaction with vinyl magnesium bromide afforded the allylic alcohol 3 followed by reaction with triethyl orthoacetate and a catalytic amount of propionic acid to form the ester 4 via the Johnson Claisen rearrangement.[15] The carbon chain of the γ,δ-unsaturated ethyl ester 4 was further extended by a four step reaction sequence, commonly used in the application of Sharpless asymmetric epoxidation (AE) to form the allylic alcohol 8.[16] The allylic alcohol 8 was converted to the epoxy alcohol 9 by Sharpless asymmetric epoxidation (AE) using diisopropyl L-tartrate (L-(+)-DIPT) as the chiral auxiliary.[17] The primary alcohol in 9 was converted to tosylate 10 which was subjected to Sharpless asymmetric dihydroxylation (ADH) by AD mix-β to form 11.[18] The camphor sulfonic acid (CSA) catalyzed epoxide ring opening and simultaneously 5-exo cyclization of 11 afforded the desired THF unit in 12. Treatment of 12 with $K_2CO_3$ in methanol afforded the expoxy THF 1.[19]

[14] Wang et.al., 1992, *Tetrahedron Lett.* 33:6407–6410.
[15] Trust et.al., 1988, *Organic Synth. Coll.* 6:606.
[16] Rossiter, B. E., Supra.
[17] Rossiter, Id.
[18] Kolb et.al., 1994, *Chem. Rev.* 94:2483–2547.
[19] See Example 1 for the data characterizing compound 1.

The specific chemical reactions and analysis were as follows:

Compound 3.

To the solution of vinyl magnesium bromide (230 mL of 1M solution in THF) in anhydrous ether (151 mL) at 0° C. was added dropwise a solution of tridecanal 2 (31.70 g, 159.8 mmol) in anhydrous THF (75 mL). After being stirred at 0° C. for 1h, the reaction was quenched by saturated $NH_4Cl$ and diluted with ether (700 mL). The organic phase was washed with water (3×160 mL) and brine (200 mL), dried over anhydrous $MgSO_4$, filtered and concentrated to give compound 3 (33.23 g, 97%) which was used for the next step without further purification. $^1H$ NMR (300 MHz, $CDCl_3$) δ 5.85 (m, 1H), 5.16 (m, 2H), 4.08 (ddd, J=6.5, 6.5, 6.5, 1H), 1.51 (m, 4H), 1.23 (m, 18H), 0.86 (t, J=6.5, 3H); $^{13}C$ NMR (75 MHz, $CDCl_3$) δ 141.27, 114.52, 73.31, 37.06, 31.94, 29.67, 29.61, 29.38, 25.36, 22.72, 14.16; IR 3347, 2926, 2856, 1468, 992, 923 $cm^{-1}$.

Compound 4.

A mixture of the allylic alcohol 3 (32.08 g, 141.1 mmol), triethyl orthoacetate (130 mL, 709 mmol) and propionic acid (1.1 mL, 15 mmol) in a round-bottomed flask equipped with a thermometer, Claisen head and condensor was heated at 138–142° C. until ethanol no longer distilled from the reaction flask (After 4 h, GC analysis indicated that no starting material 3 remained). After cooling the reaction mixture to room temperature, propionic acid and the excess triethyl orthoacetate were removed under reduced pressure to give ester 4 with a quantitative yield (41.67 g). Compound 4 was used for the next step without further purification. $^1H$ NMR (300 MHz, $CDCl_3$) δ 5.40 (m, 2H), 4.11 (q, J=7.5 Hz, 2H), 2.31 (m, 4H), 1.94 (m, 2H), 1.23 (m, 3H), 0.86 (t, J=6.5 Hz, 3H); $^{13}C$ NMR (75 MHz, $CDCl_3$) δ 173.23, 131.82, 127.84, 60.22, 34.46, 32.52, 31.94, 29.67, 29.53, 29.48, 29.38, 29.15, 27.98, 22.71, 14.28, 14.14.

Compound 5.

To the solution of ester 4 (39.59 g, 133.5 mmol) in ether (900 mL) was added LAH (7.60 g, 200 nmmol) slowly at 0° C. The reaction mixture was stirred for 3h at 0° C. and then quenched with cautious addition of water (8 mL) at 0° C. The mixture was partitioned between ether (900 mL) and water (800 mL). The organic layer was washed with saturated $NH_4Cl$ (400 mL), dried over anhydrous $MgSO_4$, concentrated. The crude product was purified by flash column chromatography (hexane/ethylacetate 4:1) to afford pure alcohol 5 (31.29 g, 92%) as a white solid. $^1H$ NMR (300 MHz, $CDCl_3$) δ 5.41 (m, 2H), 3.63 (t, J=6.5 Hz, 2H), 2.06 (m, 2H), 1.95 (m, 2H), 1.61 (m, 2H), 1.57 (m, 21H), 0.86 (t, J=6.5 Hz, 3H); $^{13}C$ NMR (75 MHz, $CDCl_3$) δ 131.24, 129.27, 62.57, 32.58, 32.46, 31.94, 29.68, 29.58, 29.38, 29.21, 28.94, 22.72, 14.16; IR (neat) 3301–3207 (br), 2998, 2954, 2917, 2848, 1461, 1367, 1060, 962 $cm^{-1}$.

Compound 6.

To a solution of oxalyl chloride (46 mL, 520 mmol) in anhydrous dichloromethane (800 mL) at −78° C. under nitrogen was added dimethyl sulfoxide (75 mL, 1.1 mol) dropwise. After stirring at −78° C. for 30 min, a solution of alcohol 5 (33.33 g, 131.0 mmol) in dichloromethane (200 mL) was added at −78° C. The resulting mixture was stirred at −78° C. for 1 h, followed by addition of triethylamine (156 mL, 1.12 mol). After being stirred for an additional 10 min at −78° C., the reaction mixture was slowly warmed to room temperature and then water (350 mL) was added. The organic layer was separated and then washed with water (2×400 mL), brine (400 mL), dried over $MgSO_4$, and concentrated to give 6 (25.62 g, 70%). The crude aldehyde 6 was dried under vacuum and used without further purification in the next step. $^1H$ NMR (300 MHz, $CDCl_3$) δ 9.74 (t, J=1.8 Hz, 1H), 5.41 (m, 2H), 2.47 (m, 2H), 2.31 (m, 2H), 1.95 (m, 2H), 1.24 (m, 19H), 0.86 (t, J=6.53 Hz, 3H); $^{13}C$ NMR (75 MHz, $CDCl_3$) δ 202.47, 132.10, 127.98, 127.51, 66.49, 43.55, 32.52, 31.94, 29.68, 29.52, 29.38, 29.17, 28.61, 28.07, 25.21, 22.72, 14.16; IR 2921, 2856, 2710, 1772, 1728, 1463, 1170, 964, 720 $cm^{-1}$.

Compound 7.

Triethyl phosphonoacetate (29.36 mL, 147.95 mmol) was added dropwise to a mixture of NaH (5.918 g of 60% dispersion in mineral oil; 147.95 mmol) in dry dimethoxy ethane (200 mL) at 0° C. under nitrogen. The resulting solution was stirred for 30 min at 0° C. and then transferred via cannula to a solution of crude aldehyde 6 (31.12 g; 123.28 mmol) in dry benzene (200 mL) at 0° C. The cooling bath was then removed and the reaction mixture was stirred at room temperature for 1 hr before being quenched with aqueous $NH_4Cl$ (100 mL) and extracted with ether (700 mL). The organic layer was washed with water (200 mL), brine (200 mL) and dried over anhydrous $MgSO_4$, filtered, concentrated and further purified by flash column chromatography (hexane/ethylacetate 50:1) to provide pure ester 7 (35.39 g, 89%). $^1H$ NMR (300 MHz, $CDCl_3$) δ 6.93 (dt, J=15.6, 6.6 Hz, 1H), 5.79 (dt, J=15.6, 1.5 Hz, 1H), 5.39 (m, 2H), 4.16 (q, J=7.2 Hz, 2H), 2.23 (m, 2H), 2.13 (m, 2H), 1.95 (m, 2H), 1.23 (m, 20H), 0.86 (t, J=6.6 Hz, 3H); $^{13}C$ NMR (75 MHz, $CDCl_3$) δ 166.66, 148.69, 131.81, 128.26, 121.44, 60.14, 32.55, 32.30, 31.94, 31.01, 29.70, 29.52, 29.38, 29.17, 22.72, 14.30, 14.16; IR 2927, 2851, 2357, 5336, 1718, 1652, 1468, 1365, 1311, 1262, 1170, 1045, 969 $cm^{-1}$.

Compound 8.

A solution of ester 7 (20.10 g, 60.45 mmol) in anhydrous dichloromethane (400 mL) was cooled to −78° C. and DIBAL-H (23.70 mL, 132.99 mmol) was added dropwise via a syringe. After stirring the reaction mixture for 1 hr, the reaction was quenched with MeOH (10 ml), warmed to ambient temperature and treated with $NH_4Cl$ (150 ml) for 30 min at 0° C. The mixture was then filtered through a pad of celite and the solid fraction was rinsed with dichloromethane (250 mL). The filtrate was washed with water (200 mL), brine (200 mL), dried over $MgSO_4$, filtered and concentrated. Flash column chromatography (hexane/ethylacetate 4:1) furnished alcohol 8 (16.25 g, 93%) as a white solid. IR (neat) 3286–3206 (br), 3000, 2954, 2917, 2848, 1471, 1442, 1080, 963 $cm^{-1}$; $^1H$ NMR (300 MHz, $CDCl_3$) δ 5.65 (m, 2H), 5.38 (m, 2H), 4.07 (m, 2H), 2.07 (m, 4H), 1.95 (m, 2H), 1.55 (bs, 1H), 1.24 (m, 20H), 0.86 (t, J=6.6 Hz, 3H); $^{13}C$ NMR ($CDCl_3$) δ 132.84, 131.10, 129.13, 63.81, 32.58, 32.32, 32.18, 31.93, 29.67, 29.54, 29.38, 29.18, 22.71, 14.15.

Compound 9.

L-(+)-diisopropyl tartrate (1.21 mL, 5.75 mmol), titanium isopropoxide (0.67 mL, 2.30 mmol), and tert-butyl hydroperoxide (14.38 mL of 5M solution in decane, 71.94 mmol) were successively added to a suspension of molecular sieves 4 Å (5g) in 200 mL of anhydrous dichloromethane and the reaction mixture was stirred at −20° C. for 25 minutes. A solution of 8 (8.07g, 28.77 mmol) in anhydrous dichloromethane (65 mL) was added to the above mixture at −30 to −25° C. The resulting mixture was stirred for 17 hours and then filtered through a celite pad. The organic phase was washed with 10% tartaric acid (180 mL), water and brine, dried over anhydrous $MgSO_4$, filtered and concentrated. Flash column chromatography (hexane/ethylacetate 1:1) provided pure compound 9 (8.02 g, 94% yield). $[\alpha]_D^{23}$−20.9° (c 0.085, $CHCl_3$); $^1H$ NMR (300 MHz, $CDCl_3$) δ 5.41 (m, 2H), 3.88 (m, 1H), 3.60 (m, 1H), 2.93 (m, 2H), 2.13 (m, 2H), 1.95 (m, 2H), 1.65–1.53 (m, 5H), 1.23 (m, 18H), 0.86 (t, J=6.6 Hz, 3H); $^{13}C$ NMR ($CDCl_3$) δ 131.61, 128.52, 61.65, 58.47, 55.52, 32.57, 31.94, 31.60, 29.69, 29.54, 29.38, 29.21, 28.99, 22.72, 14.16; IR (neat) 3191–3131(br), 2985, 2952, 2917, 2846, 1457, 1242, 1026, 985, 962, 873 $cm^{-1}$.

Compound 10.

TsCl (11.30 g, 59.32 mmol) was added to the solution of alcohol 9 (15.99 g, 53.93 mmol) and DMAP (65 mg, 5.32 mmol) in pyridine (150 mL) at 0° C. in one portion. The reaction mixture was stirred for 16 hr at 0° C. and then was quenched by pouring into a mixture of ethylacetate and water (1:1, 400 mL). The organic phase was washed with brine (40 mL), dried over $MgSO_4$, filtered and concentrated. Flash column chromatography (hexane/ethylacetate 9:1) provided the tosylate 10 (15.06 g, 62% yield). $[\alpha]_D^{23}$ −24.0° (c 0.75, $CHCl_3$); $^1H$ NMR (300 MHz, $CDCl_3$) δ 7.78 (d, J=8.0 Hz, 2H), 7.33 (d, J=8.0 Hz, 2H), 5.37 (m, 2H), 4.16 (dd, J=11.4, 4.2 Hz, 1H), 3.93 (dd, J=11.4, 6.0 Hz, 1H), 2.94 (m, 1H), 2.78 (m, 1H), 2.43 (s, 3H), 2.07 (m, 2H), 1.93 (m, 2H), 1.55 (m, 3H), 1.23 (m, 19H), 0.86 (t, J=6.5 Hz, 3H); $^{13}C$ NMR ($CDCl_3$) δ 131.80, 129.85, 128.15, 127.91, 70.13, 56.30, 54.66, 32.53, 31.93, 31.33, 29.68, 29.52, 29.38, 29.21, 28.77, 22.71, 21.69, 14.16. IR (neat) 2932, 2852, 1598, 1465, 1367,1178, 1097, 968 $cm^{-1}$.

Compound 11.

A solution of AD mix-β (15.48 g) in t-BuOH (50 mL) and $H_2O$ (50 mL) was stirred at ambient temperature for 10 min to produce two clear phases. Methanesulfonamide (950 mg, 9.98 mmol) was added and the mixture was cooled to 0° C. Compound 10 (4.98 g, 11.05 mmol) was added at once and the reaction was stirred for 20 h at 0° C. Sodium sulfite (15 g) was added and the mixture was allowed to warm to room temperature and stirred for 1h. The mixture was then partitioned between ethyl acetate and water. The organic phase was washed with brine, dried over $MgSO_4$, filtered and concentrated to give 11 (5.20 g, 97%). Compound 11 was used for the next step without further purification. $^1H$ NMR (300 MHz, $CDCl_3$) δ 7.77 (d, J=8.1 Hz, 2H), 7.33 (d, J=8.1 Hz, 2H), 4.17 (dd, J=11.4, 3.9 Hz, 1H), 3.95 (dd, J=11.4, 5.7 Hz, 1H), 3.39 (m, 2H), 2.98 (m, 1H), 2.84 (m, 1H), 2.43 (s, 3H), 1.84 (m, 1H), 1.65–1.16 (m, 17H), 0.85 (t, J=6.3, 3H).

Compound 12.

To the solution of diol-epoxide 11 (7.29 g, 15.05 mmol) in anhydrous dichloromethane (175 mL) was added camphor sulfonic acid (250 mg, 1.1 mmol) at 0° C. The reaction mixture was stirred for 30 min. The mixture was neutralized with triethylamine and partitioned between dichloromethane and water. The organic phase was washed with brine, dried over $MgSO_4$, filtered, concentrated to afford 12 which was used for next step without further purification. $^1H$ NMR (300 MHz, $CDCl_3$) δ 7.79 (d, J=8.1 Hz, 2H), 7.34 (d, J=8.1 Hz, 2H), 4.16 (dd, J=10.0, 3.0 Hz, 1H), 4.04 (dd, J=10.0, 6.0 Hz, 1H), 3.88–3.70 (m, 3H), 3.32 (m, 1H), 2.44 (s, 3H), 2.30 (m, 1H), 2.15 (bs, 1H), 2.03–1.76 (m, 3H), 1.62 (m, 1H), 1.45–1.16 (m, 22H), 0.86 (t, J=6.0 Hz, 3H); $^{13}C$ NMR (75 MHz, $CDCl_3$) δ 144.99, 132.41, 129.83, 127.89, 83.20, 78.40, 73.99, 71.38, 71.01, 33.16, 31.87, 29.61, 29.31, 28.14, 17.99, 25.50, 22.64, 21.62, 14.10; IR 3360, 2920, 2845, 1354, 1180 $cm^{-1}$.

Compound 1.

The solution of crude 12 obtained from last step in anhydrous methanol (170 ml) was treated with potassium carbonate (18.72 g, 135.46 mmol). The heterogenous mixture was stirred at ambient temperature for 1 h and then partitioned between ethyl acetate and water. The organic phase was washed with brine, dried over anhydrous $MgSO_4$, filtered and concentrated. Flash column chromatography (hexane/ethylacetate 4:1) provided pure compound 1 (3.85 g, 82% in two steps) as a white solid. $[\alpha]_D^{23}$ +71.00 (c 0.25, $CHCl_3$); $^1H$ NMR (300 MHz, $CDCl_3$) δ 3.92 (m, 1H), 3.83 (m, 1H), 3.37 (m, 1H), 2.99 (m, 1H), 2.78 (m, 1H), 2.60 (m, 1H), 2.25 (d, J=3.5 Hz, 1H), 2.11–1.94 (m, 2H), 1.84–1.63 (m, 2H), 1.50–1.16 (m, 22H), 0.86 (t, J=6.5 Hz, 3H); $^{13}C$ NMR (300 MHz, $CDCl_3$) δ 83.13, 78.50, 73.99, 53.26, 45.20, 33.52, 31.90, 29.64, 29.35, 28.40, 28.06, 25.62, 22.69, 14.13; GC/MS m/z 312 (M+), 269, 199, 143, 125, 113; IR (neat) 3473, 2923, 2854, 1466, 1070 $cm^{-1}$.

The specification recited numerous patent and literature references, each of which is hereby incorporated by reference for all purposes, as if fully set forth herein.

The invention has been described with reference to its preferred embodiements. It is understood that alternative embodiments of the invention will be obvious to one of skill in the art. All such obvious embodiments are within the spirit and scope of the invention as claimed.

We claim:

1. A stereoisomeric compound of the formula XII:

(XII)

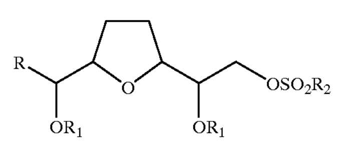

wherein R is $H_{2n+1}C_n$ and n ranges from 1 to 15;

$R_1$ is H or a hydroxy protecting group; and $R_2$ is aryl (optionally substituted with alkyl, alkoxy, halo or nitro) or alkyl.

2. The compound of claim 1, wherein n ranges from about 8 to about 15.

3. The compound of claim 1, wherein R is $H_{25}C_{12}$.

4. The compound of claim 1, wherein $R_2$ is phenyl, methyl phenyl, or lower alkyl.

5. A process for preparing a compound of formula (I), comprising the steps of:

(a) reacting a long chain aliphatic aldehyde of the formula (II)

(II)

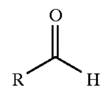

with a vinyl magnesium halide to form an allylic alcohol (III):

(III)

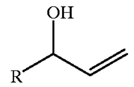

(b) reacting the allylic alcohol (III) with triethyl orthoacetate in the presence of a catalytic amount of acid to form a γ, δ-unsaturated ethyl ester of formula (IV);

(IV)

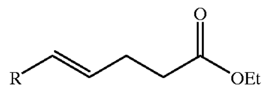

(c) extending the carbon chain of the γ, δ-unsaturated ethyl ester (IV) to form a compound of formula (VIII):

(VIII)

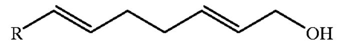

(d) converting the allylic alcohol (VIII) to an epoxy alcohol of formula (IX);

(IX)

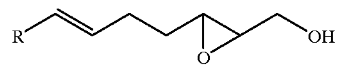

(e) converting the primary alcohol of the epoxy alcohol (IX) to a leaving group ($OSO_2R_2$) of formula (X):

(X)

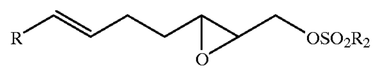

(f) subjecting (X) to Sharpless asymmetric dihydroxylation (ADH) to form the epoxide of formula (XI);

(XI)

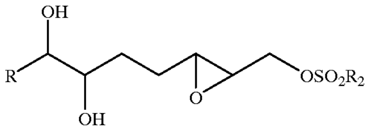

(g) opening the epoxide ring in the presence of an acid and simultaneously 5-exo cyclization of the epoxide (XI) to form the desired THF unit of formula (XII); and (XII)

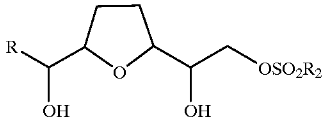

(h) treating the THF-containing compound (XII) with base to form the epoxy THF compound of formula (I):

(I)

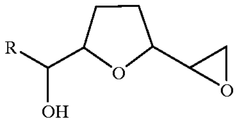

wherein R is $H_{2n+1}C_n$ and n ranges from 1 to 15; and $R_2$ is aryl or alkyl.

6. A process for preparing a compound of claim 1, comprising the steps of:

(a) converting the allylic alcohol (VIII)

(VIII)

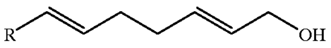

to an epoxy alcohol of formula (IX);

(IX)

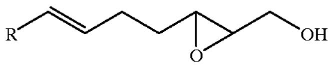

(b) converting the primary alcohol of the epoxy alcohol (IX) to a leaving group ($OSO_2R_2$) of formula (X):

(X)

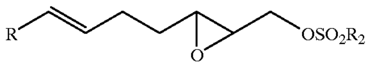

(c) subjecting (X) to Sharpless asymmetric dihydroxylation (ADH) to form the epoxide of formula (XI); and (XI)

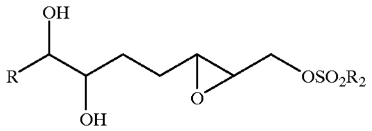

(d) opening the epoxide ring in the presence of an acid and simultaneously 5-exo cyclizaton of the epoxide (XI) to form the desired THF unit of formula (XII):

(XII)

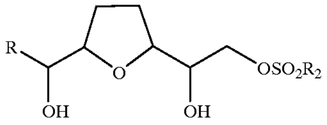

wherein R is $H_{2n+1}C_n$ and n ranges from 1 to 15; and $R_2$ is aryl or alkyl.

7. The process of claim 6, further comprising the step of:

(e) treating the THF-containing compound (XII) with base to form the epoxy THF compound of formula (I):

(I)

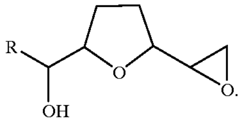

8. The process of claim 6, wherein diisopropyl L-tartrate is used as the chiral auxiliary to effect the Sharpless asymmetric dihydroxylation.

9. The process of claim 5, wherein compound II in step (a) comprises a compound where n is in the range of about 8 to about 15.

10. The process of claim 9, wherein R of compound II is $H_{25}C_{12}$.

11. The process of claim 6, wherein the primary alcohol of IX is converted to tosylate.

12. The process of claim 6, wherein camphor sulfonic acid is used to catalyze the opening of the epoxide ring.

13. The process of claim 5, wherein the leaving group of step (e) is tosylate or mesylate.

14. The process of claim 6, wherein the leaving group of step (b) is tosylate or mesylate.

* * * * *